US012575746B2

(12) United States Patent
Chung et al.

(10) Patent No.: US 12,575,746 B2
(45) Date of Patent: Mar. 17, 2026

(54) BLOOD PRESSURE MEASUREMENT DEVICE AND METHOD FOR MEASURING BLOOD PRESSURE

(71) Applicant: Guangzhou Tyrafos Semiconductor Technologies Co., Ltd., Guangzhou (CN)

(72) Inventors: Jun-Wen Chung, Tainan City (TW); Hsu-Wen Fu, Kaohsiung City (TW); Za-Hara Fu, Guangzhou (CN); Chia-Hao Chang, Taoyuan City (TW)

(73) Assignee: Guangzhou Tyrafos Semiconductor Technologies Co., Ltd., Guangzhou (CN)

( * ) Notice: Subject to any disclaimer, the term of this patent is extended or adjusted under 35 U.S.C. 154(b) by 265 days.

(21) Appl. No.: 18/494,804

(22) Filed: Oct. 26, 2023

(65) Prior Publication Data

US 2025/0040812 A1     Feb. 6, 2025

(30) Foreign Application Priority Data

Aug. 2, 2023     (CN) .......................... 202310968656.1

(51) Int. Cl.
   *A61B 5/021*     (2006.01)
   *A61B 5/00*     (2006.01)
   *A61B 5/024*     (2006.01)
(52) U.S. Cl.
   CPC ............ *A61B 5/021* (2013.01); *A61B 5/6826* (2013.01); *A61B 5/02416* (2013.01)

(58) Field of Classification Search
   CPC .... H04N 23/55; A61B 5/021; A61B 5/02416; A61B 5/6826
   See application file for complete search history.

(56) References Cited

U.S. PATENT DOCUMENTS

| | | | | |
|---|---|---|---|---|
| 10,303,921 B1 * | 5/2019 | He | ....................... | G02F 1/13318 |
| 2023/0085885 A1 * | 3/2023 | Sreeram | ................. | G06V 40/15 |
| | | | | 455/404.1 |
| 2023/0165096 A1 * | 5/2023 | Lee | .................... | A61B 5/02108 |
| | | | | 345/440.1 |

FOREIGN PATENT DOCUMENTS

| | | | | | |
|---|---|---|---|---|---|
| CN | 108182873 B | * | 8/2020 | ......... | G06V 40/1318 |
| EP | 3640778 A1 | * | 4/2020 | ............... | G06T 7/90 |

* cited by examiner

*Primary Examiner* — Gerald Johnson

(57)     ABSTRACT

A blood pressure measurement device includes a substrate, a protrusion portion, an image sensor, a first light source, a second light source, and a control and processing unit. A plurality of hollow portions is disposed within and enclosed by the protrusion portion. The first light source projects a first light toward the substrate. A finger presses the protrusion portion and the hollow portions, and the image sensor captures an image of a bright area. The control and processing unit determines whether the finger has enough pressure based on the bright area image. The second light source projects a second light toward the substrate, penetrating the substrate and the finger skin to be reflected by a blood vessel. The image sensor captures an image of a changed volume of the blood vessel, and the control and processing unit calculates the systolic or diastolic pressure.

10 Claims, 13 Drawing Sheets

31

BLOOD PRESSURE MEASUREMENT DEVICE AND METHOD FOR MEASURING BLOOD PRESSURE

CROSS-REFERENCE TO RELATED APPLICATION

This application claims the priority of Chinese patent application No. 202310968656.1, filed on Aug. 2, 2023, which is incorporated herewith by reference.

BACKGROUND OF THE INVENTION

1. Field of the Invention

The present invention relates generally to a blood pressure measurement device and method for measuring blood pressure.

2. The Prior Arts

Photoplethysmography (PPG) is a non-invasive physiological parameter measurement technology. Most wearable devices (e.g., smart watches, smart bracelets) can display real-time heart rate using photoplethysmographic sensors, and these sensors use photoelectric sensors to detect changes in tissue blood volume. However, the measurement accuracy of wearable devices is affected by noise introduced by the impact of skin contact on user or device movement, environmental conditions, and ectopic heartbeats. Therefore, the effectiveness of using wearable devices to analyze heart rate abnormalities is often limited. Thus, how to reduce the variation in skin and muscle conditions to improve accuracy is an urgent issue for improvement.

The conventional photoplethysmography device includes a photoelectric sensor and a pressure sensor. The average error value is less than 5 mmHg and the standard deviation is less than 8 mm. The reason is that: the tightness of the skin and muscle is related to the measurement accuracy of the photoplethysm wave. Therefore, the main purpose of the pressure sensor is to monitor and confirm the extent of pressure exerted by the finger to confirm the tightness of the finger skin and muscles, thereby improving the measurement accuracy of the photoplethysm wave.

However, the conventional photoplethysmography device has the following problems: first, in order to bury the pressure sensor, it cannot be manufactured on glass; second, the provision of the pressure sensor will increase the cost; third, when the photoelectric sensor and the pressure sensor are packaged in a module, the photoelectric sensor is easily contaminated and fails during the process of packaging the pressure sensor.

SUMMARY OF THE INVENTION

A primary objective of the present invention is to provide a blood pressure measurement device and method that can determine whether the pressure of finger pressing is sufficient without installing a pressure sensor.

In order to achieve the aforementioned objective, the present invention provides a blood pressure measurement device, including: a substrate; a protrusion portion, disposed on the substrate and having a plurality of hollow portions; an image sensor, disposed below the substrate and corresponds to the hollow portions; at least a first light source, disposed below one side of the substrate; at least a second light source, disposed below the substrate; and a control and processing unit, electrically connected to the image sensor, the at least one first light source, and the at least one second light source; wherein, the at least one first light source projecting a first light toward the direction of the substrate, and the first light forming a total reflection inside the substrate; when a finger presses the hollow portions of the protrusion portion, the total reflection of the first light being destroyed and reflected by the finger; the image sensor receiving the reflected first light and capturing a bright area image; the control and processing unit calculating a number of light-receiving pixels (B) based on the bright area image and a number of light-receivable pixels (A) of the image sensor, to obtain a ratio of the number of light-receiving pixels of the bright area image to the number of light-receivable pixels of the image sensor (B/A) % to determine whether the pressure exerted by the finger is sufficient; wherein, the at least one second light source projecting a second light toward the direction of the substrate; the second light penetrating the substrate and the skin of the finger and being reflected by a blood vessel; the image sensor receiving the reflected second light and capturing a blood vessel volume change image, and the control and processing unit calculating a systolic pressure or a diastolic pressure based on the blood vessel volume change image.

In a preferred embodiment, when the ratio is between 90 and 98%, the control and processing unit determines that the pressure is sufficient; wherein, when the ratio is less than 90%, the control and processing unit determines that the pressure is insufficient; when the ratio is greater than 98%, the control and processing unit determines that the pressure is too high.

In a preferred embodiment, the blood pressure measurement device further includes a reflective layer disposed between the protrusion portion and the substrate, used to prevent the path of the totally reflected first light from changing or being destroyed before entering the hollow portions.

In a preferred embodiment, the blood pressure measurement device further includes a warning unit electrically connected to the control and processing unit; wherein, when the control and processing unit determines that the pressure is insufficient or too high, the warning unit sends out a warning signal.

In a preferred embodiment, the blood pressure measurement device further includes a uniform sheet light source, disposed above the protrusion portion; wherein the uniform sheet light source projects a third light toward the direction of the substrate, and the third light passes through the hollow portions and the substrate in sequence; the image sensor receives the third light and captures an actual bright area image; and the control and processing unit determines an actual number of light-receivable pixels of the image sensor according to the actual bright area image.

In order to achieve the aforementioned objective, the present invention provides a blood pressure measurement method, which includes the following steps: when a finger presses a protrusion portion, the finger sinking into a plurality of hollow portions of the protrusion portion and pressing on a substrate; activating at least one first light source to project a first light toward the direction of the substrate, the first light forming a total reflection inside the substrate, and the total reflection of the first light being destroyed and reflected by the finger; an image sensor receiving the reflected first light and capturing a bright area image; a control and processing unit calculating a light-receiving pixel number (B) based on the bright area image, and comparing with a number of light-receivable pixels (A)

of the image sensor to obtain a ratio (B/A) % of the number of light-receiving pixels of the bright area image and the number of light-receivable pixels of the image sensor to determine whether the pressing pressure of the finger is sufficient; when the control and processing unit determines that the pressure is sufficient, activating at least one second light source to project a second light toward the direction of the substrate, and the second light penetrating the substrate and the skin of the finger and then being reflected by a blood vessel; the image sensor receiving the reflected second light and capturing a blood vessel volume change image; and the control and processing unit calculating a systolic pressure or diastolic pressure based on the blood vessel volume change image.

In a preferred embodiment, the step of determining whether the pressure pressed by the finger is sufficient further includes: when the ratio is between 90 and 98%, the control and processing unit determines that the pressure is sufficient; when the ratio is less than 90%, the control and processing unit determines that the pressure is insufficient; and when the ratio is greater than 98%, the control and processing unit determines that the pressure is too high.

In a preferred embodiment, the step of activating the at least one first light source further includes: a reflective layer being disposed between the protrusion and the substrate to prevent the path of the totally reflected first light from changing or being destroyed before entering the hollow portions.

In a preferred embodiment, after the step of determining whether the pressure pressed by the finger is sufficient, the method further includes: when the control and processing unit determining that the pressure being insufficient or too high, a warning unit sending out a warning signal.

In a preferred embodiment, before the step of pressing the protrusion with a finger, the step further includes: activating a uniform sheet light source, the uniform sheet light source projecting a third light toward the direction of the substrate and the third light passing through the hollow portions and the substrate in sequence, the image sensor receiving the third light and capturing an actual bright area image; and the image sensor receiving the third light and capturing an actual bright area image; and the control and processing unit determining an actual number of light-receivable pixels of the image sensor according to the actual bright area image.

The effect of the present invention is that the blood pressure measurement device of the present invention can determine whether the pressure of finger pressing is sufficient without setting up a pressure sensor to confirm the tightness of the finger skin and muscles, thereby increasing the photoplethysm wave measurement accuracy. Therefore, the blood pressure measurement device of the present invention can be manufactured on glass and applied to wearable devices, such as smart watches or smart bracelets, which can reduce manufacturing costs, and the image sensor does not need to be packaged in the same module as the pressure sensor. Therefore, the image sensor will not fail due to contamination.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1A:
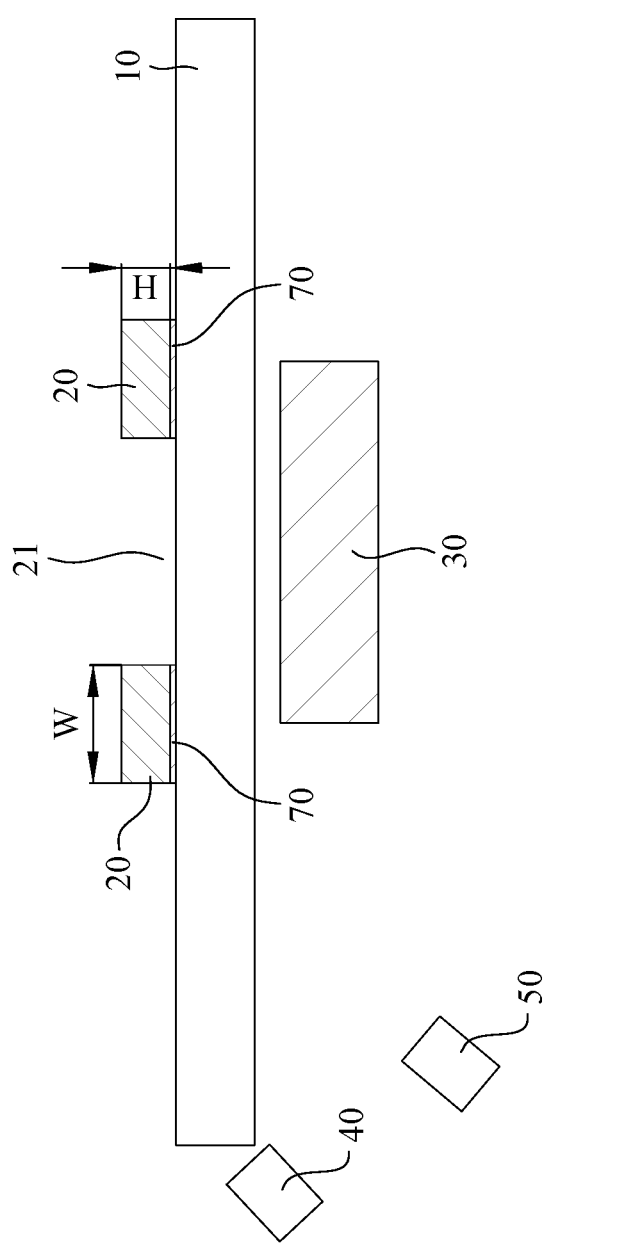
FIG. 1A is a schematic structural diagram of the first embodiment of the blood pressure measurement device of the present invention.
Figure 1B:
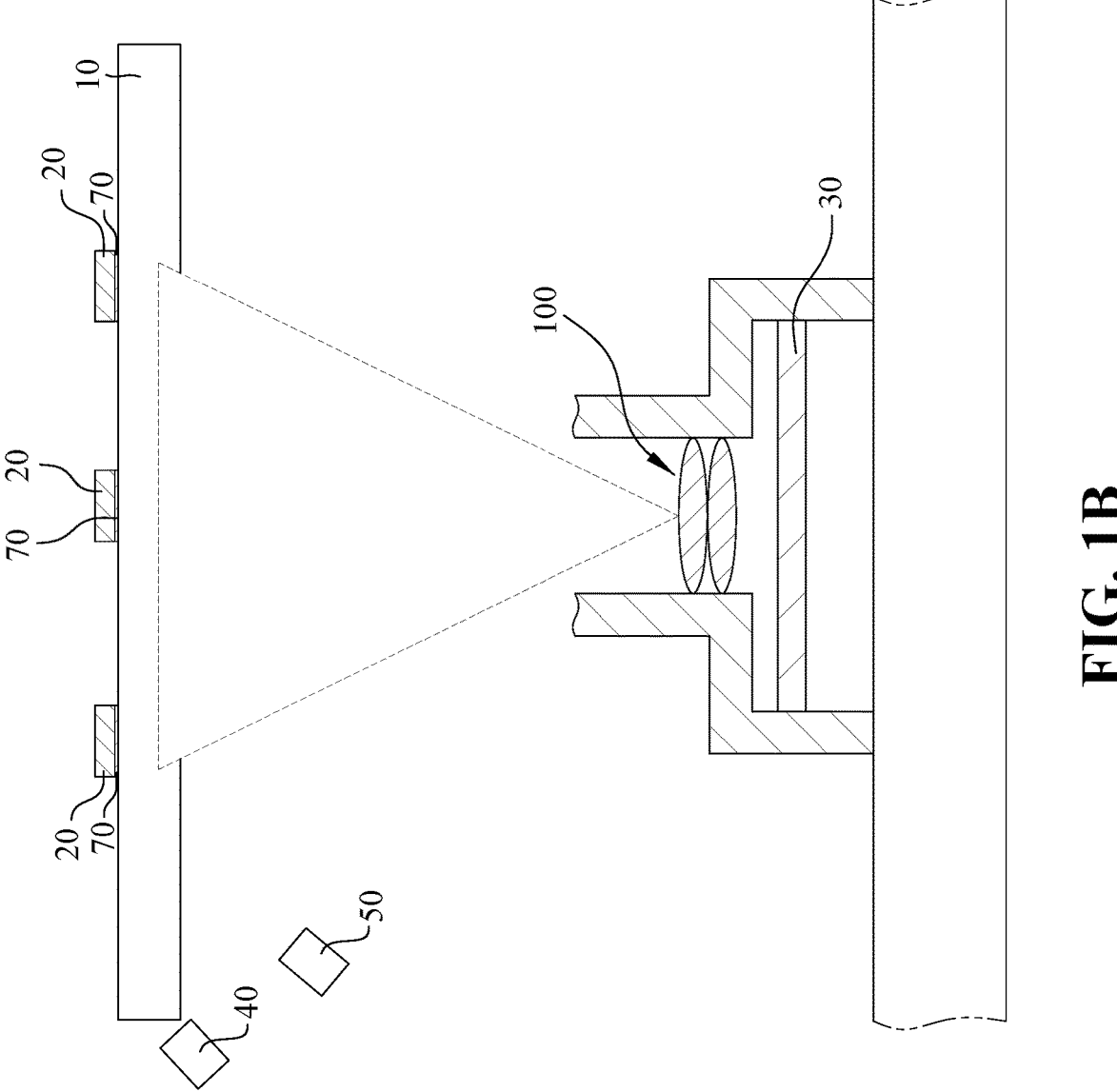
FIG. 1B is a schematic structural diagram of another embodiment of the blood pressure measurement device of the present invention.
Figure 2:
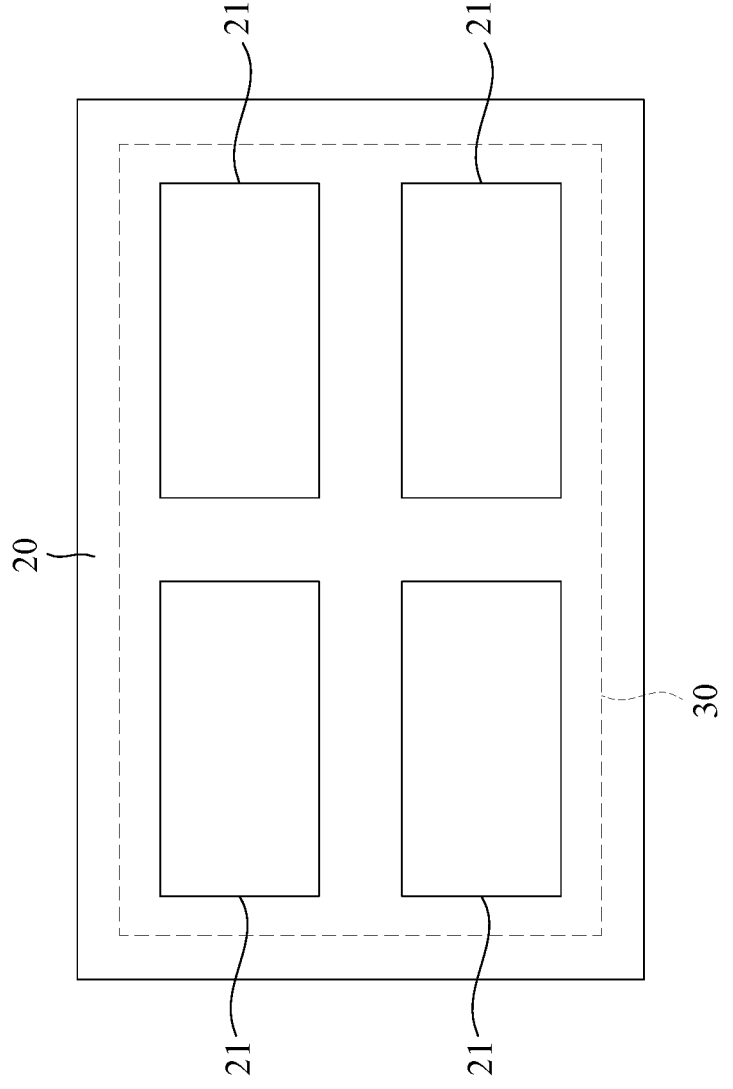
FIG. 2 is a top view of the protrusion portion and the image sensor of the present invention.
Figure 3:
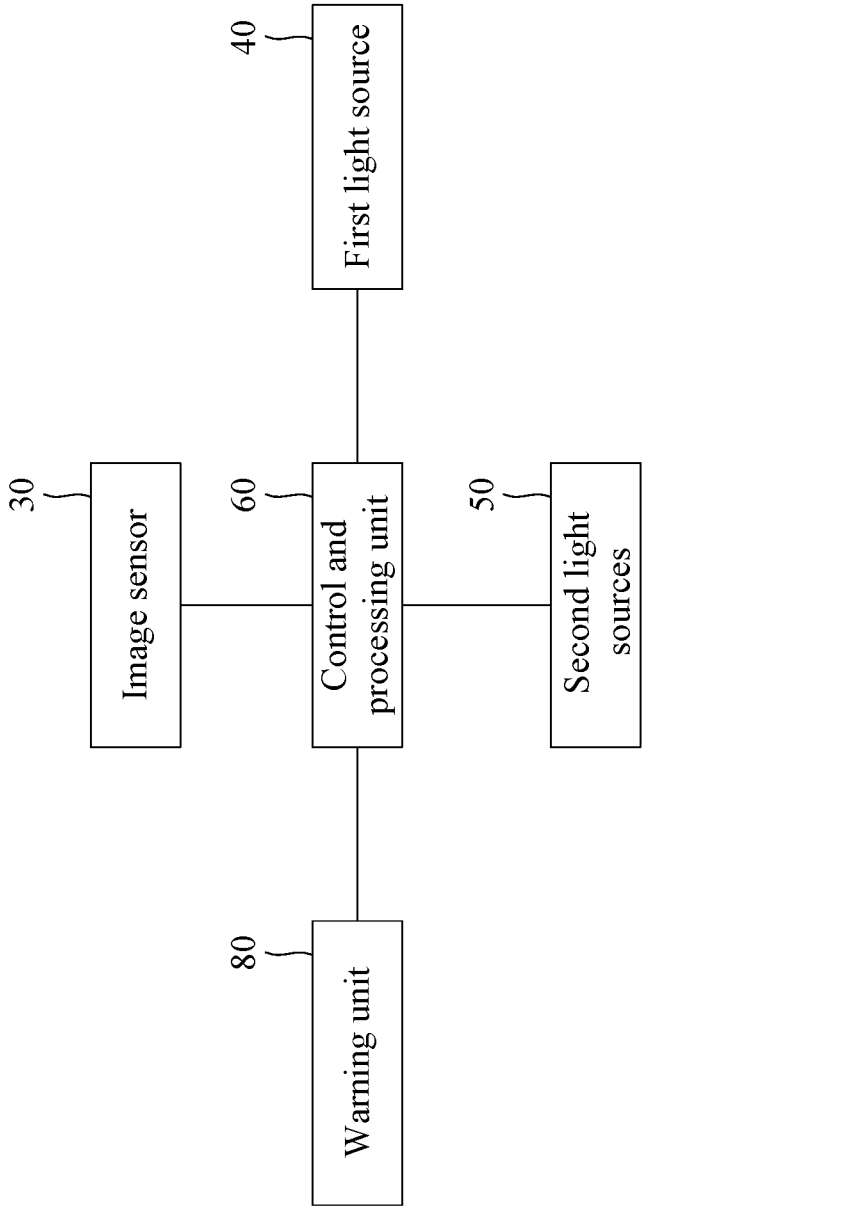
FIG. 3 is a structural block diagram of the first embodiment of the blood pressure measurement device of the present invention.

FIG. 1A is a schematic structural diagram of the first embodiment of the blood pressure measurement device of the present invention. FIG. 1B is a schematic structural diagram of another embodiment of the blood pressure measurement device of the present invention. FIG. 2 is a top view of the protrusion portion 20 and the image sensor 30 of the present invention. FIG. 3 is a structural block diagram of the first embodiment of the blood pressure measurement device of the present invention. As shown in FIGS. 1A, 1B, 2 and 3, the present invention provides a blood pressure measurement device, which includes a substrate 10, a protrusion portion 20, an image sensor 30, a first light source 40, a second light source 50, and a control and processing unit 60. The protrusion portion 20 is provided on the substrate 10 and has a plurality of hollow portions 21 formed within the protrusion portion 20 with each of the hollow portions 21 being enclosed by the protrusion portion 20 as can be seen in FIG. 2. The first light source 40 is disposed below one side of the substrate 10 and the second light source 50 is disposed below the substrate 10. The control and processing unit 60 is electrically connected to the image sensor 30, the first light source 40, and the second light source 50.

The image sensor 30 is a CMOS image sensor manufactured by a semiconductor process, and includes a plurality of unit pixels arranged in an array on a substrate. As shown in FIG. 1A, the image sensor 30 is a thin image sensor. Since the thin image sensor does not include a lens module, the thickness of the thin image sensor is smaller, but the thickness of the thin image sensor has a larger area. As shown in FIG. 1B, the blood pressure measurement device of the present invention further includes a lens module 100, and the lens module 100 is disposed between the substrate 10 and the image sensor 30. The image sensor 30 and the lens module 100 form an integrated lens-type image sensing module. Because the lens module 100 can gather light, the area of the image sensor 30 is smaller, but the thickness of the lens-type image sensing module is larger.

The control and processing unit 60 may be a microcontroller unit (MCU), including a central processing unit, a storage, a timer/counter, and a plurality of input and output interfaces.

Figure 4:
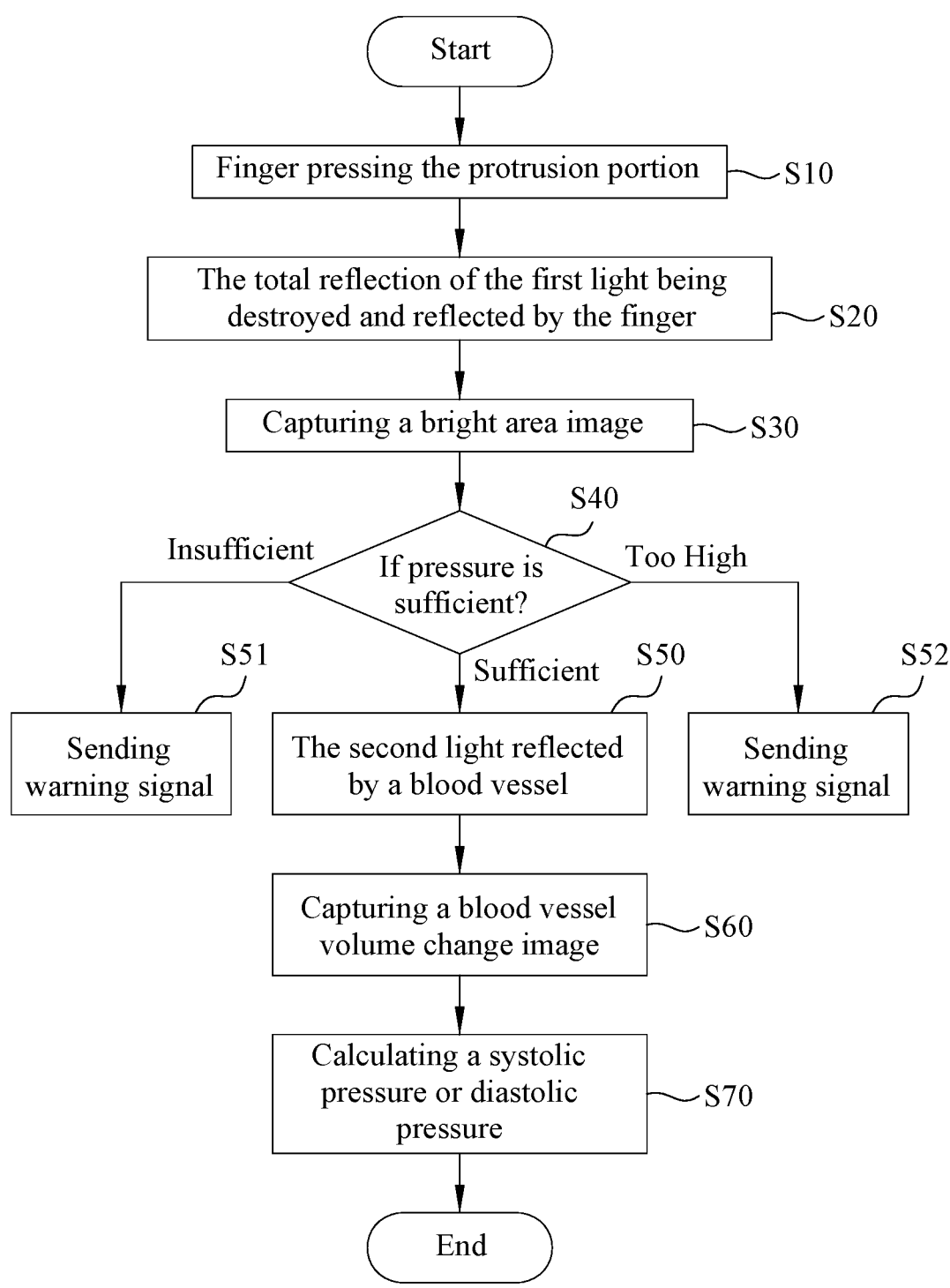
FIG. 4 is a flowchart of the first embodiment of the blood pressure measurement method of the present invention.
Figure 5:
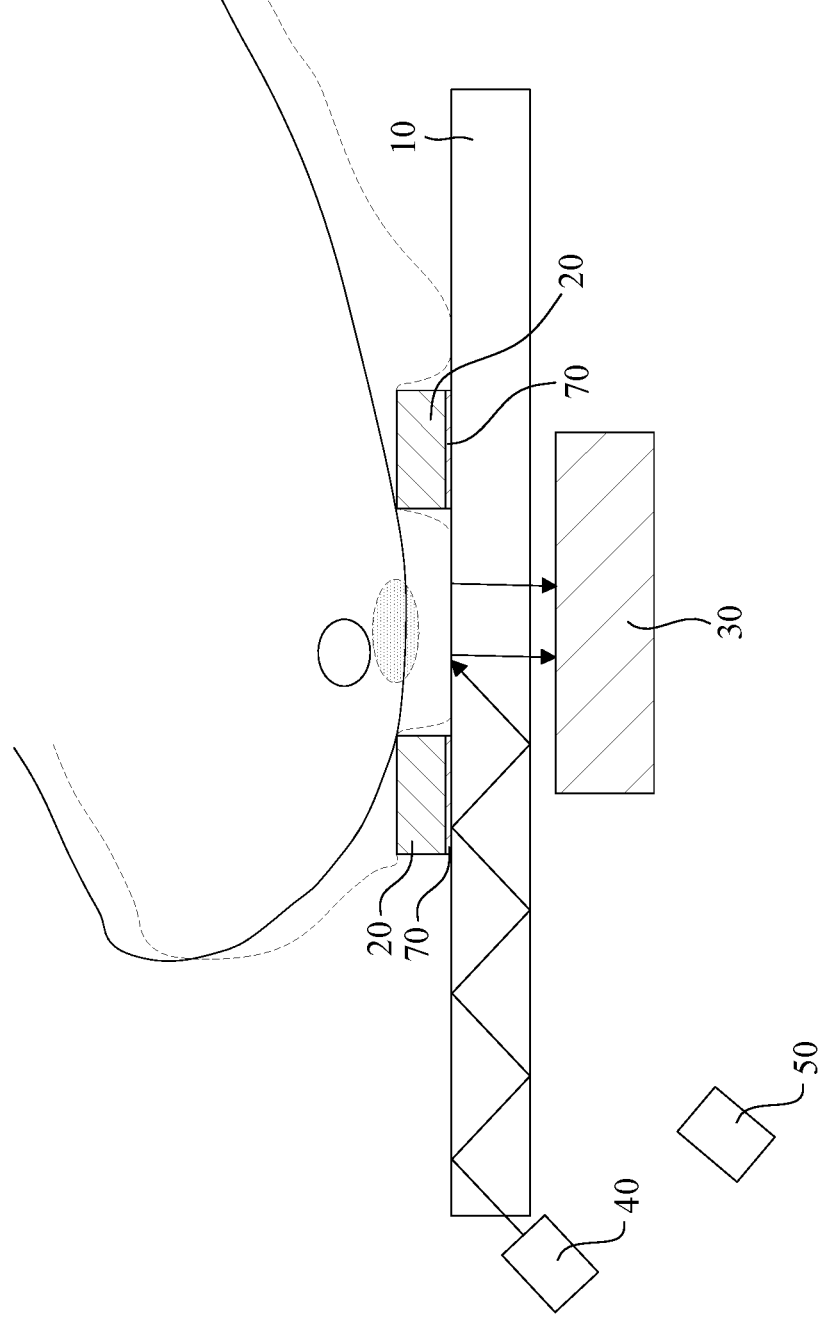
FIG. 5 is a schematic diagram of the first light projected by the first light source of the present invention being totally reflected by the substrate.
Figure 6:
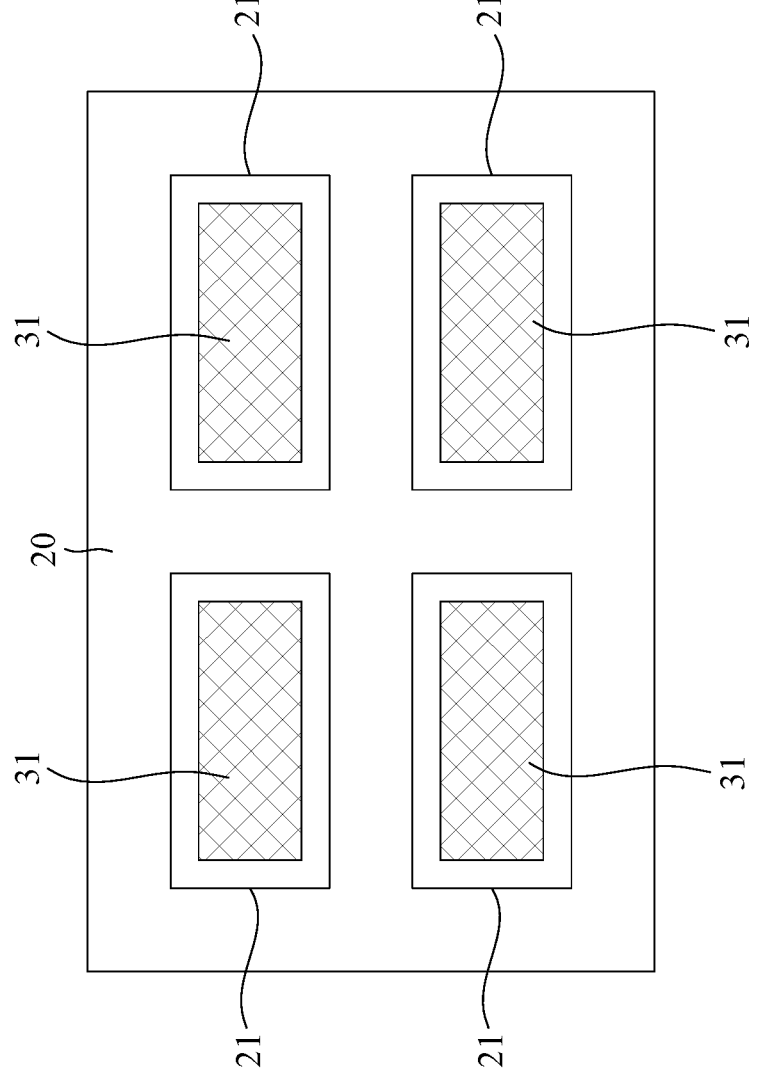
FIG. 6 shows a schematic diagram of the extent to which a finger sinks into the hollow portions.
Figure 7:
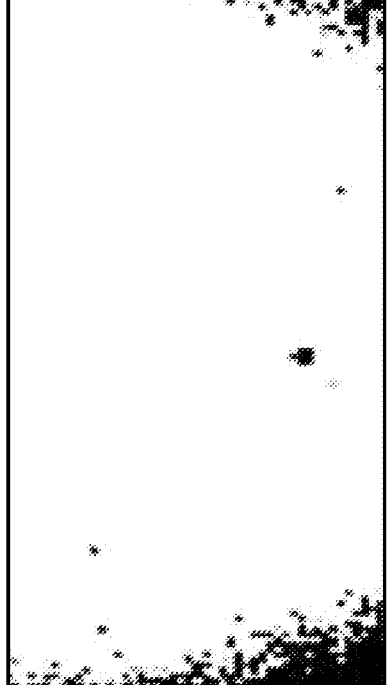
FIG. 7 shows a schematic diagram of the bright area image.
Figure 8:
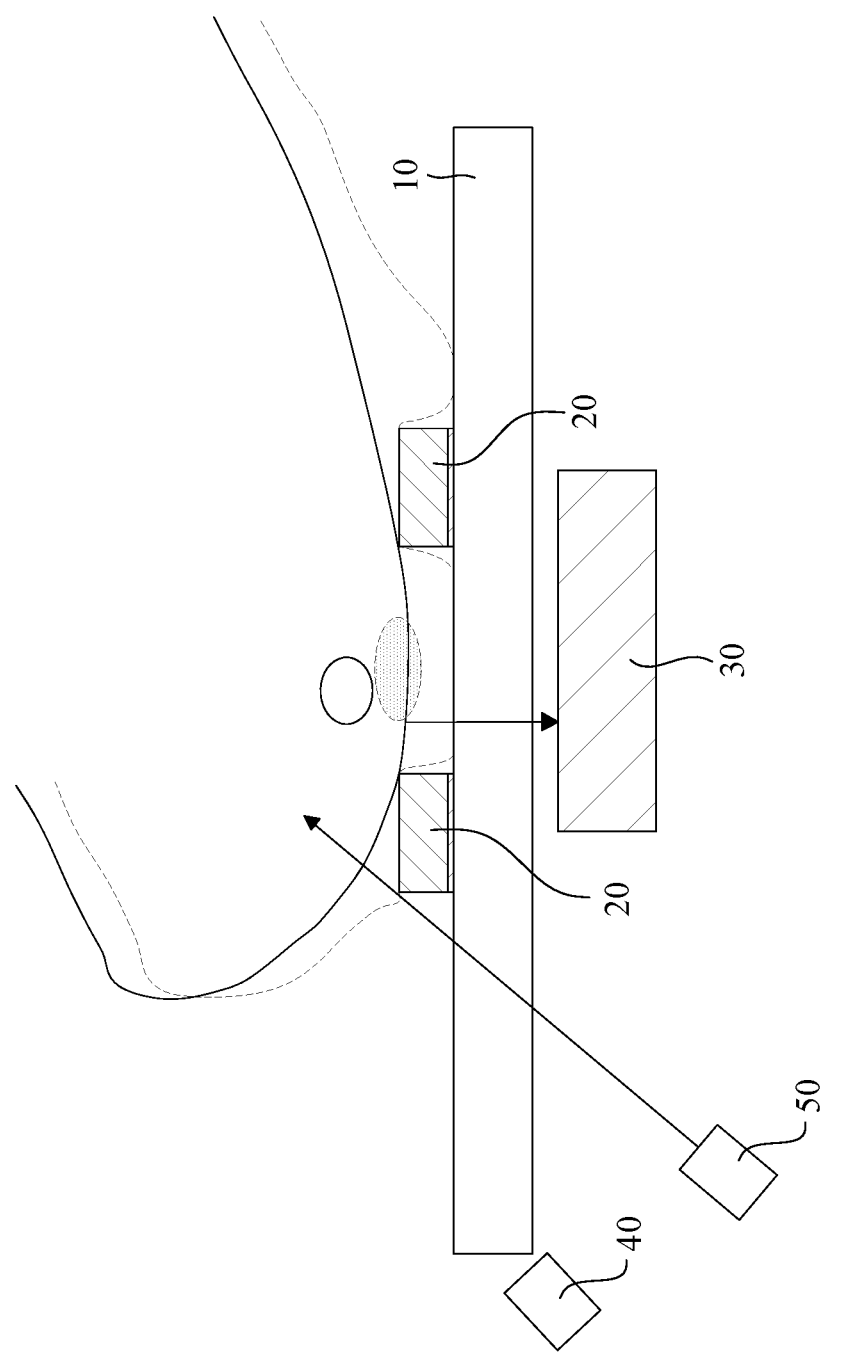
FIG. 8 is a schematic diagram of the second light projected by the second light source of the present invention being reflected by blood vessels.
Figure 9:
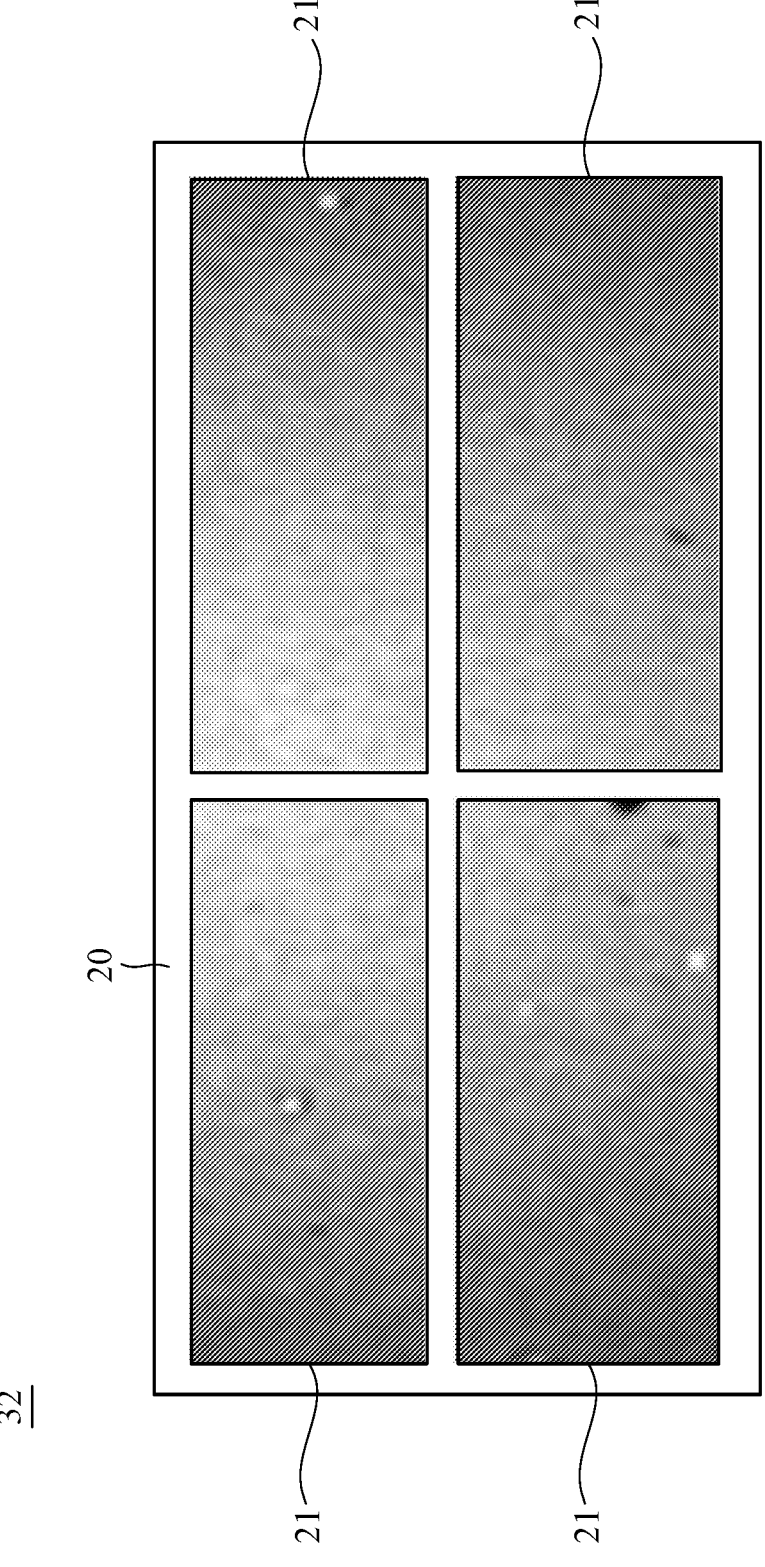
FIG. 9 shows a schematic diagram showing blood vessel volume change as systolic blood pressure.
Figure 10:
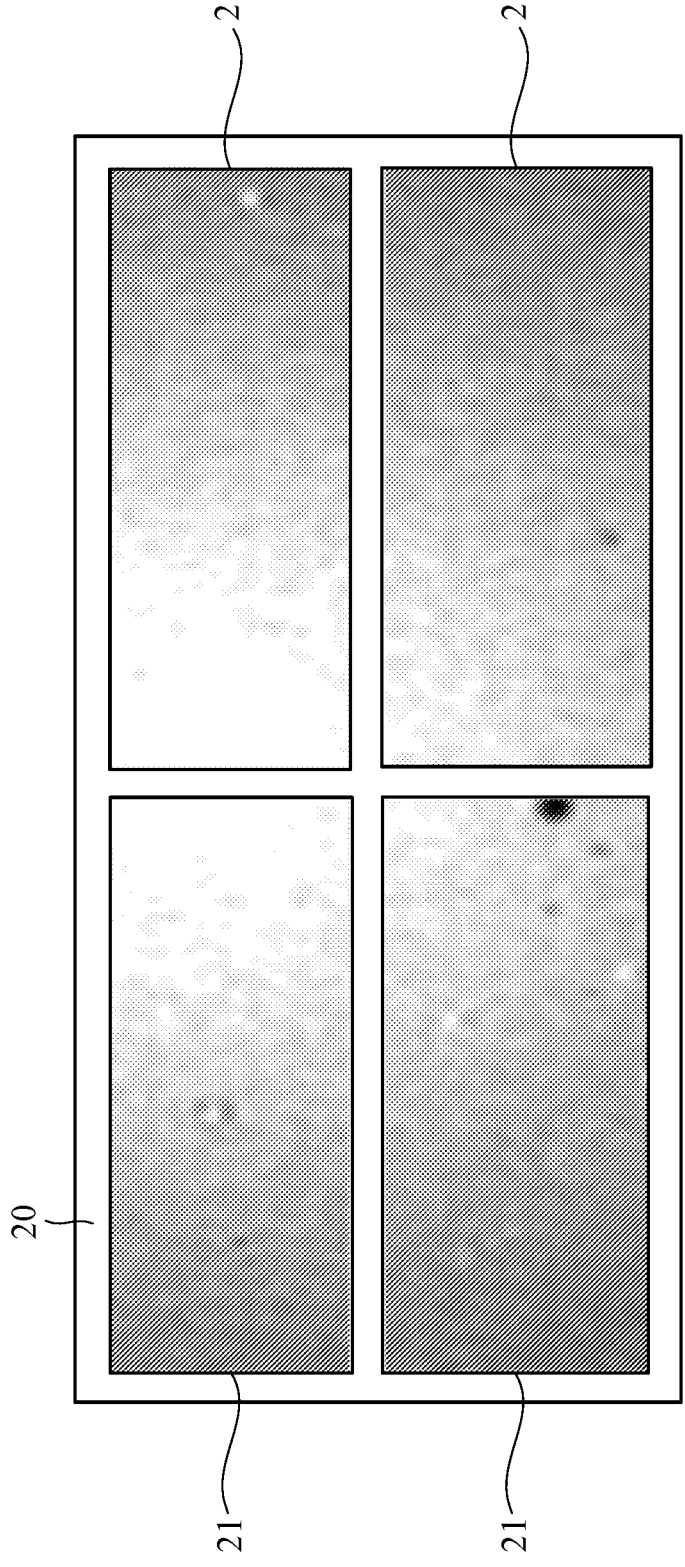
FIG. 10 shows a schematic diagram of the blood vessel volume change image as diastolic blood pressure.

FIG. 4 is a flow chart of the first embodiment of the blood pressure measurement method of the present invention. FIG. 5 is a schematic diagram of the first light projected by the first light source 40 of the present invention being totally reflected by the substrate 10. FIG. 6 shows a schematic diagram of the extent to which a finger sinks into the hollow portion 21. FIG. 7 shows a schematic diagram of the bright area image 31. FIG. 8 is a schematic diagram of the second light projected by the second light source 50 of the present invention being reflected by blood vessels. FIG. 9 shows a schematic diagram showing the blood vessel volume change as systolic blood pressure. FIG. 10 shows a schematic diagram of the blood vessel volume change image as diastolic blood pressure. The invention provides a blood pressure measurement method, which includes the following steps:

Step S10, as shown in FIGS. 4 and 5, when a finger presses the protrusion portion 20, the finger sinks into the hollow portions 21 and presses against the substrate 10.

Step S20, as shown in FIGS. 4 and 5, the first light source 40 is activated to project a first light toward the direction of the substrate 10. The first light forms total reflection inside the substrate 10. The total reflection of the first light is destroyed by the finger and is reflected.

Step S30, as shown in FIG. 4, FIG. 5, FIG. 6, and FIG. 7, the image sensor 30 receives the reflected first light and captures a bright area image 31.

Step S40, as shown in FIGS. 4, 5, 6 and 7, the control and processing unit 60 calculates the number of light-receiving pixels (B) of the bright area image 31 and the number of light-receivable pixels (A) of the image sensor 30 to obtain a ratio (B/A) % between the number of light-receiving pixels of the bright area image 31 and the number of light-receivable pixels of the image sensor to determine whether the pressure of the finger is sufficient. The number of pixels is calculated when the digital number of each unit pixel reaches a preset low threshold.

Step S50, as shown in FIGS. 4 and 8, when the control and processing unit 60 determines that the pressure is sufficient, the second light source 50 is activated to project a second light toward the direction of the substrate 10. The light penetrates the substrate 10 and the skin of the finger and is reflected by a blood vessel.

Step S60, as shown in FIGS. 4, 8, 9, and 10, the image sensor 30 receives the reflected second light and captures blood vessel volume change images 32, 33.

Step S70, as shown in FIGS. 4, 8, 9, and 10, the control and processing unit 60 calculates a systolic blood pressure or a diastolic blood pressure based on the blood vessel volume change images 32, 33.

Furthermore, as shown in FIG. 9, the blood vessel volume change image 32 is obviously darker, with a smaller bright area and a larger dark area. This is because the blood vessels are in a contracted state and the diameter of the blood vessels is small. As shown in FIG. 10, the blood vessel volume change image 33 is obviously brighter, with a larger bright area and a smaller dark area. This is because the blood vessels are in a state of relaxation and the diameter of the blood vessels is larger.

As such, the blood pressure measurement device of the present invention can determine whether the pressure of finger pressing is sufficient without setting up a pressure sensor to confirm the tightness of the finger skin and muscles, thereby increasing the amount of photoplethysm wave measurement accuracy. Therefore, the blood pressure measurement device of the present invention can be manufactured on glass and applied to wearable devices, such as smart watches or smart bracelets, which can reduce manufacturing costs, and the image sensor does not need to be packaged in the same module as the pressure sensor. Therefore, the image sensor will not fail due to contamination.

In a preferred embodiment, step S40 further includes: when the ratio is between 90 and 98%, the control and processing unit 60 determines that the pressure is sufficient; when the ratio is less than 90%, the control and processing unit 60 determines that the pressure is insufficient; when the ratio is greater than 98%, the control and processing unit 60 determines that the pressure is too high.

As shown in FIG. 1A, in a preferred embodiment, a height range H of the protrusion portion 20 is between 100 and 2000 μm, and a width range W of the protrusion portion 20 is between 300 and 2000 μm. The extent to which the fingers sink into the hollow portions 21 between the height range H and the width range W can be controlled to occupy approximately 90 to 98% of the space of the hollow portions 21, so the ratio can be controlled to be between 90 to 98%. If the height range H of the protrusion portion 20 exceeds 2000 μm and the width range W is less than 300 μm, the hollow portions 21 are too deep and too narrow. Even if the finger exerts extreme force, the finger will only sink into the hollow portion 21 to the extent of approximately less than 90% occupying the hollow portion 2, causing the ratio to be less than 90%. If the height range H of the protrusion portion 20 is less than 100 μm and the width range W exceeds 2000 μm, the hollow portions 21 are too shallow and too wide, and the fingers can easily sink into the hollow portions 21 with just a little force to occupy more than 98% of the hollow portions 21, resulting in a ratio greater than 98%.

As shown in FIG. 2, in a preferred embodiment, the number of the hollow portions 21 is four. Therefore, the square protrusion portions 20 make it easier for fingers to sink into the hollow portions 21 and press against the substrate 10.

In other embodiments, the number of the hollow portions 21 ranges from three to nine. In a preferred embodiment, because green light can penetrate the skin and be reflected by blood vessels, the second light source 50 is preferably a unit pixel of green light.

As shown in FIGS. 1A and 1B, in a preferred embodiment, in order not to affect the appearance of the smart watch or smart bracelet, the protrusion portion 20 is preferably made of a light-transmissive material, such as acrylic or glass.

As shown in FIG. 1A and FIG. 1B, in a preferred embodiment, the blood pressure measurement device of the present invention further includes a reflective layer 70 disposed between the protrusion portion 20 and the substrate 10. Step S20 further includes: as shown in FIG. 5, the reflective layer 70 is used to prevent the path of the totally reflected first light from being changed or destroyed before entering the hollow portions 21. Thereby, the reflective layer 70 can maintain total reflection of the first light inside the substrate 10, and the first light will not penetrate through the light-transmissive protrusion portion 20. Preferably, the reflective layer 70 is made of metal, such as gold, silver, aluminum, or alloys thereof.

As shown in FIG. 3, in a preferred embodiment, the blood pressure measurement device of the present invention further includes a warning unit 80, and the warning unit 80 is electrically connected to the control and processing unit 60. A step S51 is further included after step S40. As shown in FIG. 4, when the control and processing unit 60 determines that the pressure is insufficient, the warning unit 80 will send a warning signal to remind the user to increase the force of finger pressing or move the finger laterally to increase the number of light-receiving pixels of the bright area image; step S51, as shown in FIG. 4, when the control and processing unit 60 determines that the pressure is too high, the warning unit 80 will send a warning signal to remind the user to reduce the pressing force to reduce the number of light-receiving pixels of the bright area image. The warning unit 80 includes, but is not limited to, a buzzer, a voice player, and a display screen. The warning method includes, but is not limited to, sound, speech voice, light, pattern, or text. The buzzer can make a sound, and the voice player can make a speech voice. The display screen can display lights, patterns or text.

In some embodiments, the number of first light sources 40 may be plural to improve the light uniformity of the bright area image 31, but the manufacturing cost is high. However, in actual application, only one first light source 40 can achieve the above effects, and the manufacturing cost is the lowest.

In some embodiments, the number of the second light sources 50 may be plural to improve the resolution of the blood vessel volume change images 32 and 33, but the manufacturing cost is high. However, in actual application, only one second light source 50 can achieve the above effects, and the manufacturing cost is the lowest.

Figure 11:
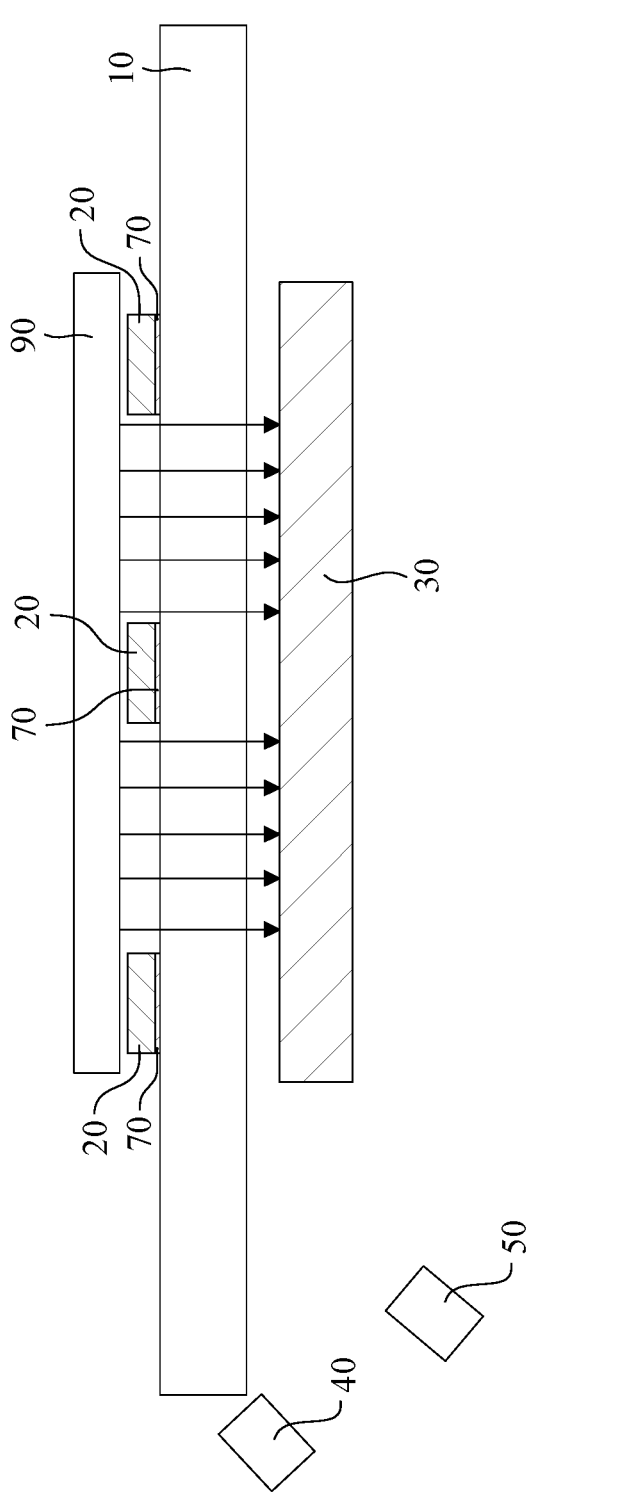
FIG. 11 is a schematic structural diagram of the second embodiment of the blood pressure measurement device of the present invention.

FIG. 11 is a schematic structural diagram of the second embodiment of the blood pressure measurement device of the present invention. As shown in FIG. 11, the structural difference between the second embodiment and the first embodiment is that the blood pressure measurement device of the present invention further includes a uniform sheet light source 90 disposed above the protrusion portion 20.

Figure 12:
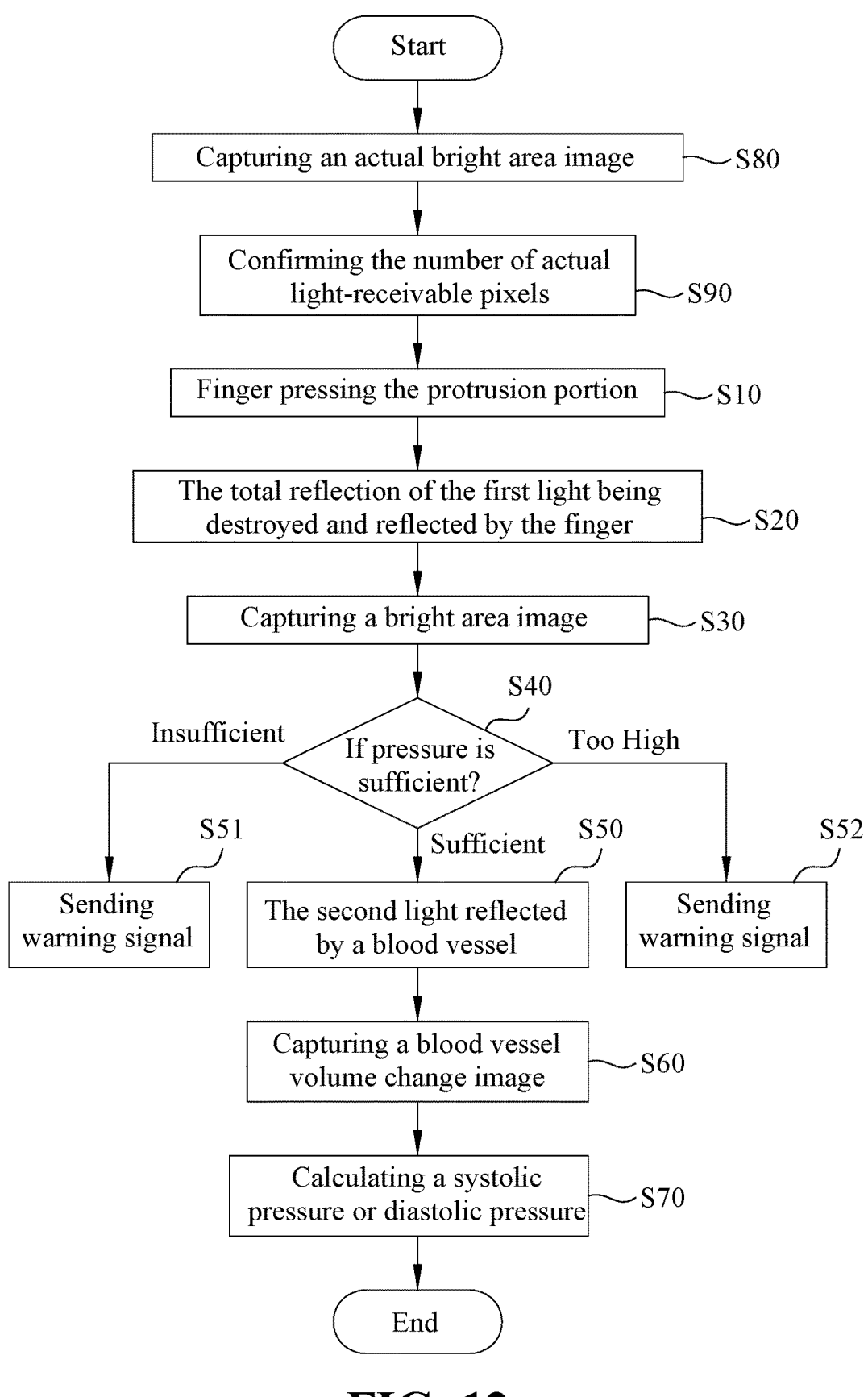
FIG. 12 is a flow chart of the second embodiment of the blood pressure measurement method of the present invention.

FIG. 12 is a flow chart of the second embodiment of the blood pressure measurement method of the present invention. As shown in FIG. 12, the difference between the method of the second embodiment and the first embodiment is that before step S10, it further includes: step S80, activating the uniform sheet light source 90 to project a third light toward the direction of the substrate 10, the third light passes through the hollow portions 21 and the substrate 10 in sequence, and the image sensor 30 receives the third light and captures an actual bright area image; and step S90, the control and processing unit 60 determines the actual number of light-receivable pixels of the image sensor 30 according to the actual bright area image. Thereby, before activating to measure blood pressure, the blood pressure measurement method of the present invention can further confirm the actual number of light-receivable pixels of the image sensor 30 through the uniform sheet light source 90, and set the actual number of light-receivable pixels of the image sensor 30 as the pressure judgment criterion of the control and processing unit 60, thereby improving the accuracy of the pressure judgment of the control and processing unit 60.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A blood pressure measurement device, comprising:
a substrate;
a protrusion portion, disposed on the substrate and the protrusion portion having a plurality of hollow portions formed within the protrusion portion with each of the plurality of hollow portions being enclosed by the protrusion portion;
an image sensor, disposed below the substrate and the image sensor corresponding to the hollow portions;
at least one first light source, disposed below one side of the substrate;
at least one second light source, disposed below the substrate; and
a control and processing unit, electrically connected to the image sensor, the at least one first light source, and the at least one second light source;
wherein, the at least one first light source projects a first light toward the substrate, and the first light forms a total reflection inside the substrate; when a finger presses the protrusion portion and sinks into the plurality of hollow portions of the protrusion portion to press against the substrate, the total reflection of the first light is destroyed and the first light is reflected by the finger; the image sensor receives a reflected first light and captures a bright area image; the control and processing unit calculates a number of light-receiving pixels (B) based on the bright area image and a number of light-receivable pixels (A) of the image sensor, to obtain a ratio (B/A) % of the number of light-receiving pixels of the bright area image to the number of light-receivable pixels of the image sensor to determine whether a pressure exerted by the finger is sufficient;
wherein, the at least one second light source projects a second light toward of the substrate; the second light penetrates the substrate and the skin of the finger and is reflected by a blood vessel; the image sensor receives a reflected second light and captures a blood vessel volume change image, and the control and processing unit calculates a systolic pressure or a diastolic pressure based on the blood vessel volume change image.

2. The blood pressure measurement device according to claim 1, wherein when the ratio is between 90 and 98%, the control and processing unit determines that the pressure exerted by the finger is sufficient; when the ratio is less than 90%, the control and processing unit determines that the pressure exerted by the finger is insufficient; and when the ratio is greater than 98%, the control and processing unit determines that the pressure exerted by the finger is too high.

3. The blood pressure measurement device according to claim 1, further comprising a reflective layer disposed between the protrusion portion and the substrate, the reflective layer being used to prevent a path of the total reflection of the first light from changing or being destroyed before the first light enters the hollow portions.

4. The blood pressure measurement device according to claim 1, further comprising a warning unit electrically connected to the control and processing unit; wherein, when the control and processing unit determines that the pressure exerted by the finger is insufficient or too high, the warning unit sends out a warning signal.

5. The blood pressure measurement device according to claim 1, further comprising a uniform sheet light source, disposed above the protrusion portion; wherein the uniform sheet light source projects a third light toward the substrate, and the third light passes through the hollow portions and the substrate in sequence; the image sensor receives the third light and captures an actual bright area image; and the control and processing unit determines an actual number of light-receivable pixels of the image sensor according to the actual bright area image.

6. A blood pressure measurement method, comprising the following steps:

preparing a substrate disposed with a protrusion portion, the protrusion portion having a plurality of hollow portions formed within the protrusion portion with each of the plurality of hollow portions being enclosed by the protrusion portion;

positioning a finger to press the protrusion portion, the finger sinking into the plurality of hollow portions of the protrusion portion and pressing against the substrate;

activating at least one first light source to project a first light toward the substrate, the first light forming a total reflection inside the substrate, and the total reflection of the first light being destroyed and the first light being reflected by the finger;

using an image sensor to receive a reflected first light and capture a bright area image;

using a control and processing unit to calculate a light-receiving pixel number (B) based on the bright area image, and compare with a number of light-receivable pixels (A) of the image sensor to obtain a ratio (B/A) % of the number of light-receiving pixels of the bright area image and the number of light-receivable pixels of the image sensor to determine whether a pressure exerted by of the finger is sufficient;

activating at least one second light source to project a second light toward the substrate when the pressure exerted by the finger is determined to be sufficient, the second light penetrating the substrate and the skin of the finger and then being reflected by a blood vessel;

using the image sensor to receive a reflected second light and capture a blood vessel volume change image; and using the control and processing unit to calculate a systolic pressure or a diastolic pressure based on the blood vessel volume change image.

7. The blood pressure measurement method according to claim 6, wherein when the ratio is between 90 and 98%, the control and processing unit determines that the pressure exerted by the finger is sufficient; when the ratio is less than 90%, the control and processing unit determines that the pressure exerted by the finger is insufficient; and when the ratio is greater than 98%, the control and processing unit determines that the pressure exerted by the finger is too high.

8. The blood pressure measurement method according to claim 6, wherein a reflective layer is disposed between the protrusion portion and the substrate to prevent a path of the total reflection of the first light from changing or being destroyed before the first light enters the hollow portions.

9. The blood pressure measurement method according to claim 6, wherein when the control and processing unit determines that the pressure exerted by the finger is insufficient or too high, a warning unit sends out a warning signal.

10. The blood pressure measurement method according to claim 6, wherein a uniform sheet light source projects a third light toward the substrate and the third light passes through the hollow portions and the substrate in sequence, the image sensor receives the third light and captures an actual bright area image; and the control and processing unit determines an actual number of light-receivable pixels of the image sensor according to the actual bright area image.

\* \* \* \* \*